(12) United States Patent
Dhyllon

(10) Patent No.: US 11,198,819 B1
(45) Date of Patent: Dec. 14, 2021

(54) FOOD WASTE CARBONIZER

(71) Applicant: Amen Dhyllon, Wynnewood, PA (US)

(72) Inventor: Amen Dhyllon, Wynnewood, PA (US)

(73) Assignee: SERENDIPITY TECHNOLOGIES LLC, Wynnewood, PA (US)

( * ) Notice: Subject to any disclaimer, the term of this patent is extended or adjusted under 35 U.S.C. 154(b) by 0 days.

(21) Appl. No.: 16/993,316

(22) Filed: Aug. 14, 2020

(51) Int. Cl.
| | | |
|---|---|---|
| C10B 53/00 | (2006.01) | |
| C10B 47/30 | (2006.01) | |
| C10B 57/10 | (2006.01) | |
| C10B 19/00 | (2006.01) | |
| C10B 57/06 | (2006.01) | |
| C12N 1/20 | (2006.01) | |
| C10B 57/14 | (2006.01) | |
| C10B 57/16 | (2006.01) | |
| C10B 31/04 | (2006.01) | |
| C12M 1/16 | (2006.01) | |
| C10B 41/00 | (2006.01) | |

(52) U.S. Cl.
CPC .............. *C10B 53/00* (2013.01); *C10B 19/00* (2013.01); *C10B 31/04* (2013.01); *C10B 41/00* (2013.01); *C10B 47/30* (2013.01); *C10B 57/06* (2013.01); *C10B 57/10* (2013.01); *C10B 57/14* (2013.01); *C10B 57/16* (2013.01); *C12M 21/16* (2013.01); *C12N 1/20* (2013.01)

(58) Field of Classification Search
CPC ........... C10B 53/00; C10B 53/02; C10B 1/10; C10B 47/30; C12M 21/16; F23G 5/027; F23G 5/0273; F23G 5/0276; C10L 5/40–48
See application file for complete search history.

(56) References Cited

U.S. PATENT DOCUMENTS

| | | | | |
|---|---|---|---|---|
| 5,407,809 | A * | 4/1995 | Finn | C12M 27/10 435/41 |
| 6,802,974 | B2 * | 10/2004 | Rebholz | C12M 43/00 210/603 |
| 9,284,203 | B2 * | 3/2016 | Josse | C02F 11/121 |
| 9,567,247 | B2 * | 2/2017 | Josse | C05F 11/00 |
| 2013/0203144 | A1 * | 8/2013 | Josse | C02F 11/10 435/167 |
| 2014/0220646 | A1 * | 8/2014 | Lim | C10G 31/10 435/134 |
| 2015/0027179 | A1 * | 1/2015 | Josse | C02F 3/12 71/10 |
| 2017/0166930 | A1 * | 6/2017 | Josse | C05F 11/00 |
| 2019/0002323 | A1 * | 1/2019 | Benedek | C02F 11/12 |

* cited by examiner

*Primary Examiner* — Jonathan Luke Pilcher
(74) *Attorney, Agent, or Firm* — Adam Warwick Bell; Matthew Rupert Kaser

(57) ABSTRACT

A high-efficiency food waste carbonization process using a carbonizer specially designed to function at a specific range of temperatures to work efficiently, with minimal energy input and designed to reduce volume and to produce charcoal that may be used as a fuel. The invention is designed to work with high-moisture materials such as food waste.

16 Claims, 3 Drawing Sheets

FOOD WASTE CARBONIZER

FIELD OF THE INVENTION

Conversion of organic matter such as food waste to a charcoal product ("bio-char")

BACKGROUND OF THE INVENTION

Organic wastes from leftover food and food processing is a continuing challenge. It tends to be heavy, have a high volume and moisture content, and decomposes rapidly to create an undesirable, odious and insanitary product. Large percentages of food intentionally prepared for consumption is wasted, with significant environmental and socio-economic implications. Food waste represents a significant fraction of municipal solid waste which is largely underutilized. It includes not only cooked foods but also fruit juices, seasoning and vegetables peels etc. Sustainable food waste management is urgently needed. Food waste is generated from domestic homes, hotels and restaurants and food processing plants at a rate of about 1 kg/person/day. Agricultural waste and food processing by products are produced at a larger rate. Much of this is disposed of in landfill. The high organic content is a huge potential source of energy but is currently wasted. Additionally, a vast amount of sewage waste is degraded using microbial processes which break down noxious elements, but produces large amounts of greenhouse gasses, while not harnessing the potential energy stored in the waste.

Organic waste is processed and disposed of in many ways such as microbial treatment, burying, dumping, compacting and burning. Pyrolysis and carbonization reduce volume and turn organic waste into useable fuel such as charcoal. Pyrolysis uses different kinds of biomass for biofuel production. In the process, organic by-products of agriculture and industry are converted into more valuable biofuel products such as solid char, liquid bio-oil, and syngas.

Production of charcoal by carbonization has been known for centuries. Charcoal production is one of the oldest chemical conversion processes known to mankind Even today, charcoal production continues on a large scale worldwide using tradition charcoal kilns. Carbonization is the conversion of organic matter into low-moisture carbon substances through heating the organic matter in an environment with limited amounts of oxygen present. This process 'cracks' large molecules and is used to produce charcoal, coke, coal gas, coal tar, ammonia liquor, and "coal oil". Typically, carbonization is done by heating biomass in an oxygen-free or oxygen-limited environment, with reaction conditions tailored to maximize the production of char.

Although there has been a great deal of recent interest in hydrothermal carbonization (HTC), this disclosure focuses on dry carbonization, which is faster and more efficient than HTC. Dry carbonization has been used to carbonize all sorts of biomaterials such as organic wastes from food processing and sewage sludge. Dry carbonization is performed at temperatures of 200-700° C. to produce biochar (also called pyrochar).

In some applications carbonization converts biomass into biochar and syngas, which is a fuel gas mixture consisting primarily of hydrogen, carbon monoxide, and carbon dioxide and is used in creating synthetic natural gas and for producing ammonia or methanol. For dry carbonization, the amount of heat applied controls the degree of carbonization and the residual content of foreign elements. For example, at 1200 K, the carbon content of the residue exceeds a mass fraction of 90 wt %, whereas at 1600 K, more than 99 wt % carbon is found. Carbonization is often exothermic, which means that it could in principle be made self-sustaining and be used as a source of energy that does not produce carbon dioxide.

BRIEF DESCRIPTION OF THE INVENTION

The present invention may be used to carbonize food and food-processing waste, and agricultural bio-waste such as wood, coconut shell, palm shell, rice husk, sawdust, bagasse, straw, bamboo, as well as sewage sludge.

An object of the present invention is to provide a rapid, efficient and economical process for converting biomass into charcoal. It is a further object of the present invention to provide a pyrolytic process that is self-sustaining and, once running, does not require the input of energy from an external source. It is a further object of the present invention to reduce the required external heat input for converting biomass into charcoal. It is a further object of the present invention to provide heat energy by virtue of an exothermic pyrolytic reaction.

The key advantage of the present invention is that the process is very efficient and using the appropriate combination of steps, temperatures and times, and using both heat and plasma, the carbonization process may be carried out with the carbonization stage lasting less that than 8 hours, and whereby at least 90% of the food waste is fully carbonized.

Energy input is required to begin the reaction, but at some stage the reaction becomes exothermic and produces enough heat to be self-sustaining without the need for external energy input. In various embodiments the invention utilizes plasma contained within the carbonization chamber.

The invention comprises an enclosed chamber (a "carbonization chamber" or "drum") adapted to accept and contain food waste. The chamber must be effectively airtight, able to withstand an internal vacuum, and thermally insulated. The drum includes a feeder hatch (for input of materials), and a disgorgement hatch, for emptying (which may be the same as the feeder hatch). Inside the chamber are, optionally, baffles (or any dimension or shape) adapted to aid in mixing of the materials therein. The drum is adapted to rotate so as to mix the contents.

Various elements may be included within the chamber including, for example, an element for heating the contents, i.e., a heat source or vent or duct or element; an element for exposing the contents to light such as a light source such as a UV light source; a plasma generating element such as a nitrogen plasma jet assembly.

Other elements may be attached to the drum, such as lines (pipes) for the introduction and extraction of gasses or liquids, such as the introduction of nitrogen gas to displace oxygen and aid in drying, or the extraction of water or water vapor.

Within the chamber the method is carried out comprising the following steps:
1) Initial biological degradation.
2) Drying under vacuum.
3) Carbonization.

It is an objective of the present invention to provide a waste treatment process, equipment, and materials, which require a relatively small investment, low operating cost, requires minimal labor and energy. It is an objective of the present invention to provide a waste treatment process that is versatile, that can work with high moisture organic materials, and can be done in a single chamber. The process is carbon neutral and environmentally friendly and produces high quality carbon, which can be used or sold as a source of energy. Objects and advantages to the present invention will be readily apparent upon reference to the drawing and the following description.

DETAILED DESCRIPTION OF THE INVENTION

Figure 1:
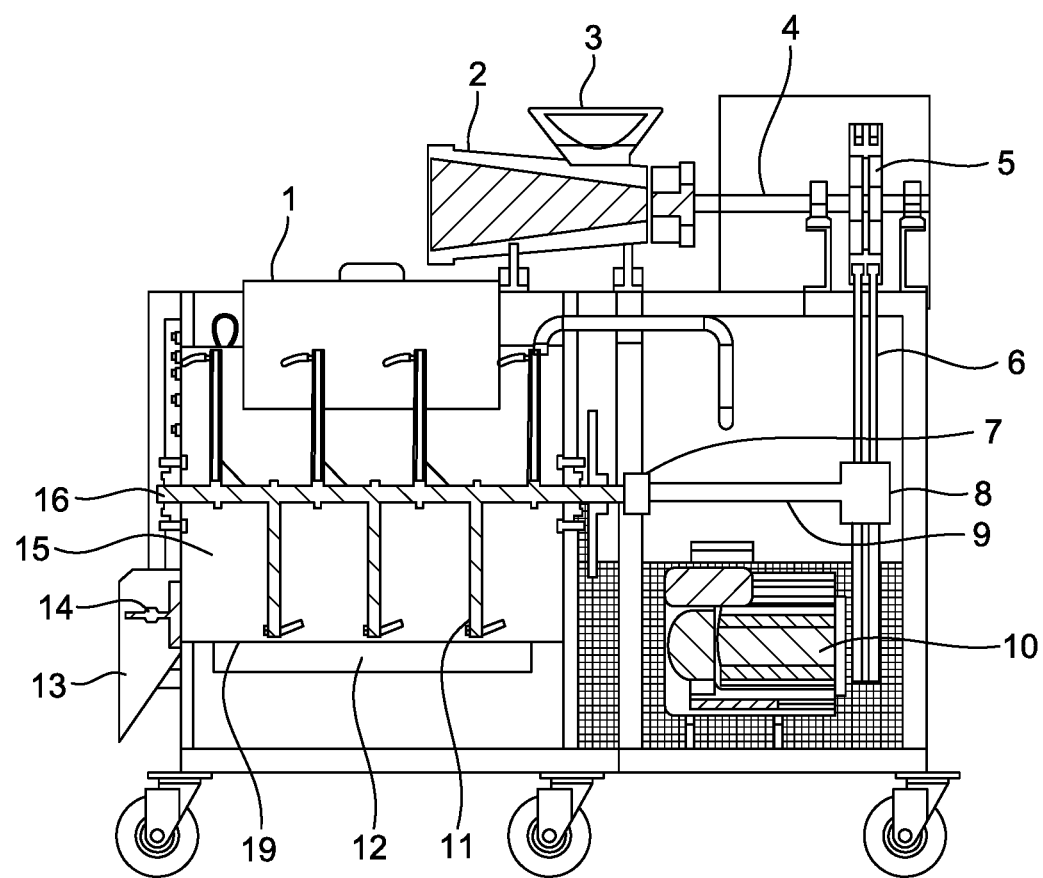
FIG. 1 Left hand side view of carbonizer machine
FIG. 2 Rear view of carbonizer machine
FIG. 3 Top view of carbonizer machine
Figure 2:
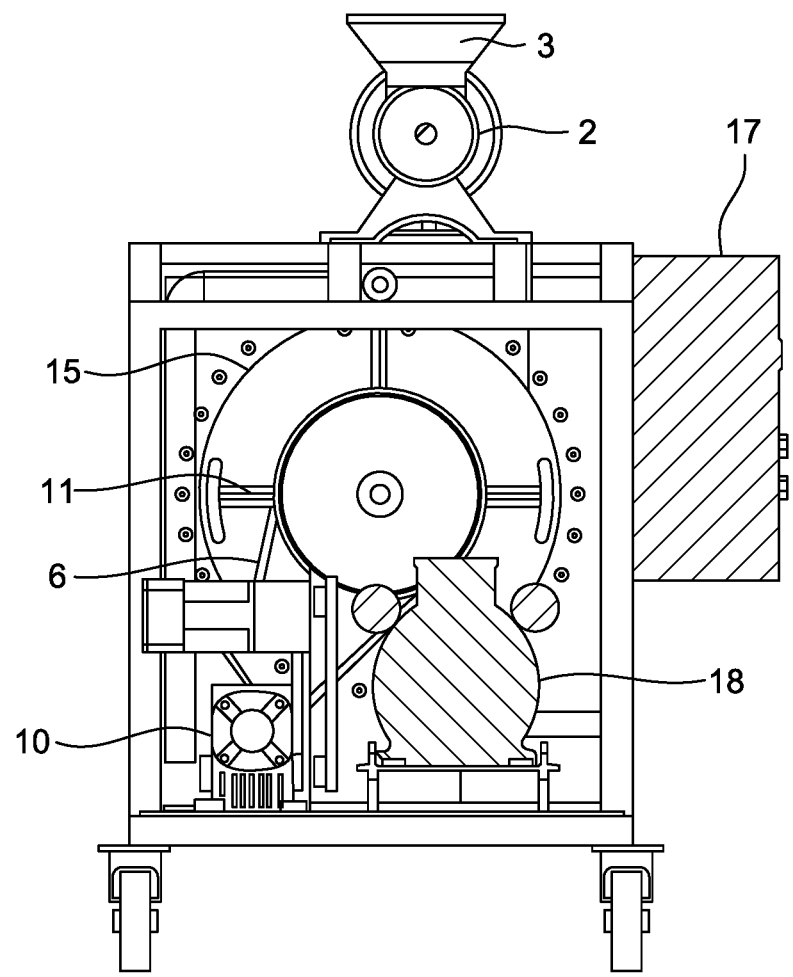
Figure 3:
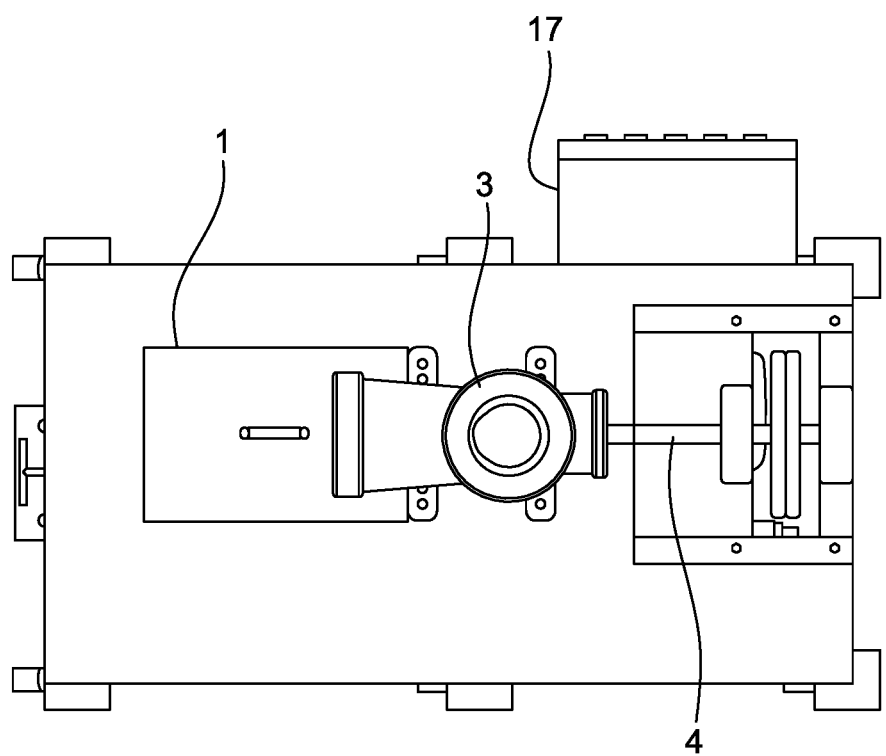

The present solution is a high-efficiency food waste carbonization process using a carbonizer specially designed to function at a specific range of temperatures to work efficiently, with minimal energy input and designed to reduce volume and to produce charcoal that may be used as a fuel. The invention is designed to work with high-moisture materials such as food waste.

Objects and Advantages of the Invention

The key advantage of the present invention is that the process is very efficient and using the appropriate combination of steps, temperatures and times, and using both heat and plasma, the carbonization process may be carried out with the carbonization stage lasting less that than 8 hours, and whereby at least 90% of the food waste is fully carbonized. In some embodiments 80% carbonization is achieved with the carbonization stage lasting less than an hour. In some embodiments 85% carbonization is achieved with the carbonization stage lasting less than two hours. In some embodiments 85% carbonization is achieved with the carbonization stage lasting less than two hours. In some embodiments 90% carbonization is achieved with the carbonization stage lasting less than three hours. In some embodiments 95% carbonization is achieved with the carbonization stage lasting less than four hours. At least 98% or 99% carbonization may be achieved with the carbonization stage lasting less than four-and-a-half hours.

The most efficient process of the invention uses a nitrogen plasma generator functionally connected to the drum wherein nitrogen plasma is used both to break down organic material before the fermentation stage and also during the carbonization heating stage. Maximum efficiency is achieved using a bacterial culture of *Bacillus subtilis* and/or *Pseudomonas* species, with the fermentation time is between 1 and 2 days, wherein the drying temperature is between 300° C. and 350° C. and wherein, during carbonization, the interior of the drum is heated to between 900° C. and 1100° C. and a plasma is introduced into the drum during the process.

Method Embodiments

The method embodiments the invention encompasses a method comprising the following steps: 1) Initial biological degradation. 2) Drying under vacuum. 3) Carbonization.

1) Initial Biological Degradation.

Place organic materials in container, and apply heat (about 37° C. to 42° C., but no higher than 46° C. Add an inoculate of bacteria and mix into the materials contained in the container. Aerate and ferment with the inoculate of bacteria for a period of between 5 and 100 days.

For example, the invention may use the potent bacterial isolates of *Bacillus subtilis* (e.g. B1U/1 and D3L/1) and/or *Pseudomonas* species (e.g. RAT/5). Heat should be maintained at between 37° C. and 45° C. during fermentation. Constant aeration may be achieved by rolling in a drum. The drum may be the same drum as the carbonization chamber and indeed the entire method may be done in the one single chamber. Common organic wastes can be composted using the selected isolates individually, and the C/N ratio of each substrate reduced gradually in a period of time from 1 day to 120 days. The method provides optimization of the composting process prior to drying and carbonization.

2) Drying Under Vacuum.

After biological degradation, dry under vacuum and heat above 50° C. For example, in a preferred embodiment, heat continuously for between 1 hour and 20 hours, for example between 2 and 10 hrs or between 3 and 8 hrs or between 5 and 7 hrs. Preferably heat to a temperature that does not cause combustion, but encourages drying, for example to 250° C., or between 350° C. and 450° C. E.g., 350° C. for 6 hours under partial vacuum.

Vacuum is provided by a standard vacuum pump. The drying process is carried out in the same container, i.e., the carbonization chamber. Drying under vacuum or in an atmosphere of nitrogen reduces oxidation and combustion and increases carbonization. The drum may be purged with nitrogen after the fermentation process. Or the drum may be evacuated to a low partial pressure of air, for example 0.1, 0.2, 0.4, 0.5 or 0.6 atmospheres. Vacuum is provided by a standard vacuum pump. The drying process is carried out in the same container, i.e., the carbonization chamber. In some embodiments, the reaction becomes exothermic and produces enough heat to be self-sustaining. In some embodiments the invention utilizes plasma contained within the carbonization chamber.

3) Carbonization.

After drying, heat the interior of the food waste carbonizer to an optimum temperature between 300° C. and 500° C. to promote pyrolysis and production of charcoal. An optimal temperature for the process is 300° C. The carbonization process may be catalyzed with catalyst added to the mixture, or present in or on the interior walls of the carbonization chamber. For example the catalyst may be a di carboxylic acid or tricarboxylic acid or sulfuric acid, or may be a metal such as palladium, rhodium, platinum or AlCl3-HCl catalyst, or sulfonated porous carbon catalyst (0.5 g), 20 wt. % NaCl, and water-ethyl acetate biphasic solvent at ratios of 1:2. This process may be done under a partial vacuum (less than 1 bar, for example 0.85, 0.75, 0.5, 0.25 or 0.1 bar). Nitrogen may be introduced to reduce oxygen in the atmosphere and increase carbonization efficiency. The drum may be purged with nitrogen after the fermentation process. Or the drum may be evacuated to a low partial pressure of air, for example 0.1, 0.2, 0.4, 0.5 or 0.6 atmospheres. Other inert gasses may be used to displace the oxygen such as xenon, helium, neon, argon, or krypton.

A nitrogen plasma may be used to enhance breakdown of various organic compounds in a low-oxygen environment, thereby enhancing breakdown and carbonization. Plasma may be used after of before the biodegradation/fermentation step and/or during the carbonization step. Nitrogen plasma may be made by various know means such as excitation of Nitrogen by a microwave discharge at about 2450 MHz-200/W in a fused silica tube. Some examples may use a nitrogen plasma jet.

In other embodiments Hydrothermal Carbonization may be used. This method may be coupled with anaerobic digestion (AD) in the present method. Hydrothermal carbonization (HTC) can be used to enhance the biomethane potential during anaerobic digestion (AD) of the organic fraction of municipal solid waste (OFMSW). The use of HTC liquid and slurry into AD leads to an increase in biomethane production up to 37% and 363%, respectively, compared to OFMSW. Methane production increases as the HTC process severity decreased, reaching its maximum at 180° C., 1 h for both HTC products. Combustion of biogas produced by AD of HTC liquid and slurries covers up to 30% and 104% of the HTC thermal demand, respectively. When the energy from hydrochar and biogas combustion is recovered, the process efficiency reaches 60%, making HTC coupled with AD a very efficient system.

A magnetic field oxygen-concentration system can be used in certain embodiments to help remove oxygen from the carbonization chamber. In certain embodiments, magnetic confinement may be used to contain the plasma within the carbonization chamber.

The carbonization stage may last for less than 30 minutes, less than 60 minutes, less than 2, 3, 4, 5, 6, 7, 8, 9, 10, 11, 12 hrs or less than 15 hrs with carbonization of at least 70%, 80%, 85%, 90%, 95% and 98%.

SPECIFIC EXEMPLARY METHODS OF THE INVENTION

The inventor has found that combining the steps of biological degradation using specific organisms, drying under vacuum or flooded with nitrogen, and carbonization using catalysis, very efficient carbonization occurs.

Example 1

Step 1: Initial biological degradation. Load organic waste materials in drum-shaped container, and heat, aerate and ferment with an inoculate of bacteria. Mix and heat to a temperature of between 25° C. and 45° C. for between 1 and 7 days, preferably rom 2-4 days. Mixing and aeration is achieved by rolling in a drum with internal baffles.

Step 2: Drying under vacuum. After biological degradation (step 1), evacuate or partially evacuate the drum to between 0.01 and 0.50 atmospheres. Dry the contents of the drum under vacuum and heat. Heat for between 2 and 84 hours at a temperature between 100° C. and 450° C.

Step 3: Carbonization. After drying, maintain a vacuum or flood the drum with an inert gas such as nitrogen, and heat the interior of the carbonizer drum to a temperature between 300° C. and 1200° C. to promote production of charcoal.

Step 4: Cool and disgorge the charcoal product. Grind and form into briquettes for commercial sale and use.

Example 2

Step 1: Initial biological degradation. Load organic waste materials in drum-shaped container comprising internal baffles, and heat, aerate and ferment with an inoculate of bacteria, wherein the bacterial isolates comprise *Bacillus subtilis* (e.g. B1U/1, D3L/1) and/or *Pseudomonas* species (e.g. RAT/5). Mix and heat to a temperature of 42° C. for 5 days. Mixing and aerate by rolling drum.

Step 2: Drying under vacuum. After biological degradation (step 1), partially evacuate the drum to 0.2 (+/−0.2) atmospheres. Dry the contents of the drum under vacuum and heat. Heat for between 2 and 84 hours at a temperature between 250° C. and 350° C.

Step 3: Carbonization. After drying, maintain a vacuum or flood the drum with an inert gas such as nitrogen, and heat the interior of the carbonizer drum to a temperature between 300° C. and 1200° C. to promote production of charcoal.

Step 4: Cool and disgorge the charcoal product. Grind and form into briquettes for commercial sale and use.

Example 3

Step 1: Initial biological degradation. Load organic waste materials in drum-shaped container comprising internal baffles, and heat, aerate and ferment with an inoculate of bacteria, wherein the bacterial isolates comprise *Bacillus subtilis* (e.g. B1U/1, D3L/1) and/or *Pseudomonas* species (e.g. RAT/5). Mix and heat to a temperature of 42° C. for 5 days. Mixing and aerate by rolling drum.

Step 2: Drying under vacuum. After biological degradation (step 1), partially evacuate the drum to 0.2 (+/−0.2) atmospheres. Dry the contents of the drum under vacuum and heat. Heat for between 24 and 48 hours at a temperature between 250° C. and 350° C.

Step 3: Carbonization. After drying, maintain a vacuum or flood the drum with an inert gas such as nitrogen, introduce a catalyst into the drum, and heat the interior of the carbonizer drum to a temperature between 800° C. and 1200° C. to promote production of charcoal. In example 3, the carbonization process is catalyzed with catalyst added to the mixture or present on the interior walls or baffles of the carbonization chamber. For example the catalyst may be a di-carboxylic or tricarboxylic acid or sulfuric acid, or may be a metal such as palladium. Or in an alternative embodiment, catalysts are used that comprise a catalytic system a mixture of titanium dioxide nanoparticles and sodium dodecylsulfate in water Step 4: Cool and disgorge the charcoal product. Grind and form into briquettes for commercial sale and use.

Example 4

Step 1: Initial biological degradation. Load organic waste materials in drum-shaped container, and heat, aerate and ferment with an inoculate of bacteria. Mix and heat to a temperature of between 25° C. and 45° C. for between 1 and 7 days, preferably rom 2-4 days. Mixing and aeration is achieved by rolling in a drum with internal baffles.

Step 2: Drying under vacuum. After biological degradation (step 1), evacuate or partially evacuate the drum to between 0.01 and 0.50 atmospheres. Dry the contents of the drum under vacuum and heat. Heat for between 2 and 84 hours at a temperature between 100° C. and 450° C.

Step 3: Carbonization. After drying, pressure in the drum is increased, not decreased. The pressure is between 5 and 9 bar. The interior of the carbonizer drum is maintained between 300° C. and 1200° C. to promote production of charcoal. Carbonization is achieves within 72 hrs.

Step 4: Cool and disgorge the charcoal product. Grind and form into briquettes for commercial sale and use.

Example 5

In an alternative embodiment, in the carbonization step to remove moisture, sodium borohydride powder and helium gas may be injected into the carbonization chamber. The sodium borohydride reacts with the water inside the carbonization chamber, thereby generating hydrogen.

Example 6

In an alternative embodiment, either prior to or after the fermentation step and/or during the carbonization step, plasma is created from air within the carbonization chamber by subjecting the air to sufficient electrical energy so that plasma is created.

Example 7

In an alternative embodiment, either prior to or after the fermentation step and/or during the carbonization step, nitrogen plasma is introduced into the carbonization chamber. It may be vented in from an external nitrogen plasma source such as a plasma jet.

Example 8

In an alternative embodiment, before Step 1, chemical breakdown is increased by providing electrical discharges within the carbonization chamber using electrodes placed inside the chamber. The electrodes are positioned to extend from the outside of the carbonization chamber to the inside and may be made of graphite to prevent contamination of the carbon product. An electric current may be introduced by use or a ring electrode or brushes making contact with the electrodes on the outside of the carbonization chamber.

Example 9

In an alternative embodiment, before Step 1, efficiency of chemical breakdown is increased by using microwave radiation, or UV radiation or x-ray radiation within the carbonization chamber.

Example 10

A high-efficiency food waste carbonization process comprising the following steps:
(a) providing a carbonization device, the device comprising a filling hopper for providing feedstock to a drum, the drum defining an interior chamber surrounded by a heat insulating layer and having a door for filling and disgorging contents, the drum having interior baffles to aid mixing contents, whereby the drum is connected to a rotating drive shaft and the drive shaft is connected via a belt or gears to a motor, and where the drum additionally has functionally attached thereto, input lines for introducing fluid substances and output lines for extracting fluid substances, whereby the drum is effectively airtight when in use except for the intentional introduction and extraction of fluids via the input lines and output lines, and wherein the device additionally includes a heating source for providing heat to the interior of the drum, and a thermal probe within the drum to monitor the internal temperature, which thermal probe is functionally connected to a thermostatic control unit which controls heat input and regulates interior temperature of the drum, and whereby the device additionally includes a heat transfer system for transferring heat away from the drum and transferring said heat to an electric generator;
(b) loading food waste materials through the door into a drum
(c) inoculating the food waste with a defined bacterial culture
(d) rotating the drum and heating and fermenting the contents at a temperature of between 25° C. and 45° C. for between 1 and 7 days;
(e) using a vacuum pump to create a vacuum or partial vacuum within the drum
(f) maintaining a vacuum or partial vacuum within the drum between 0.01 and 0.50 atmospheres (g) drying the contents of the drum under vacuum and heat for between 2 and 84 hours at a temperature between 100° C. and 450° C.
(h) continuing to maintain a vacuum within the drum or flooding the drum with nitrogen
(i) heating the interior of the drum to a temperature between 300° C. and 1200° C. to promote production of charcoal, and maintaining this temperature for between 1 and 72 hours
(j) cooling the drum and disgorging the charcoal product
(k) grinding and charcoal product and forming it into shaped briquettes.
wherein the device further comprises a nitrogen plasma generator functionally connected to the drum, wherein at stage (c) the bacterial culture comprises *Bacillus subtilis* and/or *Pseudomonas* species, wherein the fermentation time is between 2 and 4 days, wherein in step (g) the drying temperature is between 300° C. and 350° C., wherein a plasma is introduced into the drum after stage (b) and before stage (c), and also during stage (i), and wherein in step (i) the interior of the drum is heated to between 900° C. and 1100° C., and wherein the fermentation stage of step (d) lasts less than 72 hours, and the heating of step (i) is carried out for less than 4 hours, and whereby at least 95% of the food waste is fully carbonized.

Further Methods of the Invention

The invention also includes various specific methods of efficiently making charcoal from bio-waste. One such method comprises: a) drying the waste by exposing said waste to a pressure of at least 3 bar, and a temperature of at least 250° C.; b) releasing the water vapor out of the carbonization chamber, and; c) carbonizing at least partially the waste by maintaining said waste during a period of time of at least 5 minutes to a pressure of at least 3 bar, and a temperature of at least 250° C., thereby obtaining carbon; and d) optionally separating non-organic material from the obtained carbon.

Another such method comprises: a) drying the waste by exposing said waste to a vacuum of at least 0.5 bar or less, and a temperature of at least 250° C.; b) releasing the water vapor out of the carbonization chamber, and; c) carbonizing the waste by maintaining said waste during at least 24 hours at a pressure of at least 3 bar, and a temperature of at least 250° C., thereby obtaining carbon; and d) optionally separating non-organic material from the obtained carbon.

Another such method comprises: a) drying the waste by exposing said waste to a temperature of at least 350° C. under vacuum or a nitrogen atmosphere; b) carbonizing the waste by maintaining said waste for at least 24 hours at a temperature of at least 350° C., thereby obtaining carbon.

The process may be done under a partial vacuum (less than 1 bar, for example 0.85, 0.75, 0.5, 0.25 or 0.1 bar). Nitrogen may be introduced to reduce oxygen in the atmosphere and increase carbonization efficiency.

The carbonization step may also be performed under pressure, where the temperature reaches 350 to 450° C., even up to 500° C., and the pressure is at least 3 bar, preferably 8 bar, more preferably 9 bar or more. A flash point is reached and the molecules that make up the waste material are cracked to transform the waste into carbon. As long as the temperature and the pressure are maintained at the required levels, the carbonization process starts and takes from 5 to 35 minutes.

In an alternative embodiment, in the carbonization step to remove moisture, sodium borohydride powder and helium gas may be injected into the carbonization chamber. The sodium borohydride reacts with the water inside the carbonization chamber, thereby generating hydrogen.

In one embodiment, during the carbonization stage, increased gas pressure is used to increase efficiency of carbonization. In such an embodiment, air pressure inside the carbonization chamber, which is substantially air-tight in use, is increased above atmospheric pressure by use of an external pump. Pressure may be increased to, for example, 2, 3, 5, 7, 12 or 15 times atmospheric pressure. The chamber is flooded with nitrogen or evacuated, and being air-tight, any oxygen present is soon combined with the contents in the chamber, leading to increased canbonization efficiency. Nitrogen or another inert gas may be introduced into the chamber throughout the process. Other inert gasses may be used to displace the oxygen such as xenon, helium, neon, argon, or krypton.

In another embodiment, air pressure inside the carbonization chamber is decreased below atmospheric pressure by use of a vacuum pump. This reduces oxygen content, reduces combustion, and increases carbonization and charcoal production. This method is useful for large volume carbonization chambers.

In another embodiment, electro-magnets may be placed in proximity to the air inlets, which magnets or electro-magnets will create a paramagnetic effect and concentrate the atmospheric oxygen which can be vented away from the chamber, increasing the proportion of nitrogen.

In one embodiment, rapid removal of moisture is achieved by using a vacuum created within the carbonization chamber. This is particularly useful with slurries and effluent waste carbonization.

In one embodiment, plasma is created from air within the carbonization chamber by subjecting the air to sufficient electrical energy so that plasma is created. A plasma with a temperature as low as 5 eV can have a sufficient number of electrons above 15.6 eV to produce a weakly ionized plasma. This corresponds to about 55,000 degrees Kelvin.

In another embodiment, nitrogen plasma is introduced into the carbonization chamber. It may be vented in from an external nitrogen plasma source such as a plasma jet.

In one embodiment, efficiency of combustion and chemical breakdown is increased by providing electrical discharges within the carbonization chamber using electrodes placed inside the chamber. The electrodes are positioned to extend from the outside of the carbonization chamber to the inside and may be made of graphite to prevent contamination of the carbon product. However, at suggested operating temperatures electrodes of steel, platinum or other like compounds may be used. An electric current may be introduced by use or a ring electrode or brushes making contact with the electrodes on the outside of the carbonization chamber.

In one embodiment, efficiency of chemical breakdown is increased by using microwave radiation, or UV radiation or x-ray radiation within the carbonization chamber.

In one embodiment high pressure air jets are placed within the carbonization chamber to increase particularization of the contents and increase efficiency of combustion and chemical destruction.

In one embodiment, grinding plates and/or venturi mixing is used to grind and mix the contents of the carbonization chamber to increase breakdown of contents.

In one embodiment high pressure jets of an air/sand mixture are used within the carbonization chamber to increase structural breakdown.

In another embodiment lime, alkali and other caustic substances are introduced into the carbonization chamber to speed up chemical breakdown. Chlorines and other oxidizing substances may also be used.

In various embodiments a combination of heat and pressure may be used to speed up decomposition.

In a preferred embodiment, the carbonization chamber is air-tight or substantially air-tight when in use. This prevents oxygen entering the chamber and increases efficiency of carbonization.

In other embodiments the carbonization chamber includes vents that can allow gasses to enter or exit the carbonization chamber.

In some embodiments an exhaust vent is present that allows exhaust gasses to exit the device. In various embodiments, activated carbon can be used in the exhaust path to capture odors produced during the process. In other embodiments a condenser is used to convert gasses into bio-oil.

Further methods of the invention (here written in claim format) that may be pursued in related applications include the following:

1. A method for transforming waste into carbon in a carbonization chamber, said method comprising: a) drying the waste by submitting said waste to a pressure of at least 3 bar, and a temperature of at least 250° C.; b) releasing the water vapor out of the carbonization chamber, and; c) carbonizing at least partially the waste by maintaining said waste during a period of time of at least 5 hours to a pressure of at least 3 bar, and a temperature of at least 250° C., thereby obtaining carbon; and d) optionally separating non-organic material from the obtained carbon.

2. The method according to claim 1, wherein in step a) and in step c), said pressure is, each independently, at least 4 bar, at least 5 bar, at least 6 bar, at least 7 bar, at least 8 bar, at least 9 bar, or at least 10 bar.

3. The method according to claim 1 or 2, wherein in step a) and in step c), said temperature is, each independently, at least 275° C., at least 300° C., at least 325° C., or at least 350° C.

4. The method according to any one of claims 1 to 3, wherein in step c), said period of time is at least 7 minutes, at least 10 minutes, at least 15 minutes, or at least 20 minutes.

5. The method according to any one of claims 1 to 4, wherein said method, after the carbonizing step c), further comprises depressurizing and cooling at a temperature below 100° C.

6. The method according to any one of claims 1 to 5, wherein the temperature of at least 250° C. is supplied by a heating means and a catalytic system.

7. The method according to claim 6, wherein the catalytic system comprises i) at least one nanofluid aqueous solution and ii) at least one thermal conductive gas supplied into the carbonization chamber.

8. The method according to claim 7, wherein the at least one thermal conductive gas is selected from helium, hydrogen, $CO_2$, CO, argon, ethylene, HCl, $H_2S$, neon, and any combination thereof.

9. The method according to claim 7 or 8, wherein the at least one nanofluid aqueous solution is obtained by mixing titanium dioxide nanoparticles and sodium dodecylsulfate in water.

10. The method according to any one of claim 7 or 8, wherein the at least one thermal conductive gas is a non-explosive mixture of hydrogen and helium, and the hydrogen is supplied into the carbonization chamber by means of a hydride powder.

11. A carbonization chamber for transforming organic material or waste into carbon according to any one of claims 1 to 10.

12. A catalytic system comprising i) at least one nanofluid aqueous solution and ii) at least one thermal conductive gas as defined in any one of claim 8 or 10.

13. The method according to any one of claims 1 to 10, wherein the waste is selected from municipality solid waste, hospital waste, drugs, slaughterhouse waste, sludge collected from sewage, and industrial organic waste.

14. The method according to any one of claim 1 to 10 or 13, wherein the waste comprises non-organic material such as metal or glass.

15. The method according to any one of claim 1 to 10 or 13 or 14, wherein at least a portion of the obtained carbon is recycled to heat the carbonization chamber.

16. The carbonization chamber according to claim 1 1 wherein said carbonization chamber further comprises an inlet for supplying the at least one thermal conductive gas as defined in any one of claim 8 or 10, and an outlet for releasing the water vapor.

17. The carbonization chamber according to claim 1 1 or 16, wherein said carbonization chamber further comprises a heating system, a cooling system, an air-pressure system, a security valve, and one or two doors.

ADDITIONAL ELEMENTS OF VARIOUS DEVICE EMBODIMENTS

The invention encompasses a device, which is the food waste carbonizer in which food waste is carbonized using the method of the invention. The carbonized material is ground and briquetted to form solid fuel that has commercial value for example as a fuel for cooking, barbequing, hot water production, boiler fuel etc.

The device is a carbonization chamber preferably shaped as a drum, comprising a combined filling hopper and grinder (2) for providing feedstock to the carbonization chamber which comprises a drum (16) defining an interior chamber, surrounded by a heat insulating layer (19), having a door (lid) (1) wherein the chamber has baffles/impellers (11) on the inside of the drum to aid in mixing. The drum is connected to a rotating drive shaft (9) driven by a motor (10). The drum additionally may have an outlet/exit hatch (11) for collecting charcoal from the carbonization chamber. The drum additionally has, functionally attached thereto, input lines (tubes, pipes) for introducing fluid substances and output lines (tubes, pipes) for extracting fluid substances (liquids and gasses and vapors). The drum may be heated from an internal or external heating element. A heating element/assembly (12) may be positioned within the drum, for example against the interior walls of the drum. The heating element may provide heat via an electric resistance element or by burning a gas or oil or other combustible liquids or gasses. The drum may additionally comprise a plasma generating assembly unit such as a hydrogen plasma jet (18). A thermal probe is provided within the drum to monitor the internal temperature. This may be functionally connected to a thermostatic control unit/control assembly (17) which sends feedback to a heating control unit which controls the heat input. Carbonization is an exothermic process and heat may be derived from the drum by means of a liquid cooling system comprised of pipes conducting a coolant liquid. Water or other coolant passing through the pipes is boiled to produce steam which is fed into a generator to produce electricity. Alternatively the heated water may be maintained under pressure as a liquid and used to generate heat via an electrical thermocouple generator.

In a preferred embodiment, the interior of the carbonization chamber/drum (16) is coated with retractile coating and/or catalytic materials of, for example, graphite and/or zirconia oxide, to minimize heat loss and increase efficiency of conversion of organic waste to charcoal with minimal heat input. This increases the output yield by at least 20% compared with a carbonization chamber not coated with graphite and/or zirconia oxide.

The carbonizer may be run at any temperature above 250° C., such as 300° C., 400° C., 500° C., 600° C., 700° C., 800° C., 900° C., 1000° C., 1200° C., 1300° C. or between 900 and 1700° C. Between temperature of 230° C. and 250° C., depolymerizations take place and long chain polymers are broken into short chain of hydrocarbons. Running the food waste carbonizer at an optimum temperature between 300° C. or 500° C. promotes pyrolysis and produces an optimum charcoal yield. Depending on the time of exposure and type of waste, and temperature between 300° C. and 500° C. is considered optimal for certain embodiments, and efficiency or carbonization. At lower pyrolysis temperatures (300° C.) the process converts up to 90 wt % of the original organic solids to charcoal.

In a specific, preferred embodiment, the invention is the machine as shown in the figures.

The Carbonizer machine in an exemplary embodiment has a 25 kg/cycle capacity, suitable for commercial kitchens. The target temperature within the carbonization chamber is 300° C. The carbonization chamber is coated with a refractile mixture of graphite and zirconia oxide.

Running the food waste carbonizer at an optimum temperature between 300° C. or 500° C. promotes pyrolysis and produces an optimum charcoal yield. At 300° C., the molecular bonds between carbon and other elements such as oxygen and hydrogen are broken and carbon char is produced Operational parameters for this embodiment are:
Capacity: 50 kg-1000 KG/day
Per load: 5 hours (1 hour cooling)
Material: Kitchen waste (Organic/Degradable)
Heating: 3 kW (Heating system: Heater band)
Process time: 5 hours, operating temperature
Power: 280-300 C, Single phase
Power: 3 kW The figures illustrate various aspects of the Food Waste Carbonizer. It is not limited to the embodiment shown in the figures. Variations are also contemplated as being within the scope of the claims, as will be readily apparent to those having ordinary skill in the art after becoming familiar with the teachings herein.

In the example, the carbonization chamber includes a cylindrical drum comprised of walls and bottom coated with a refractile mixture of graphite and zirconia oxide. The drum includes an openable lid. The lid has a planar circular shape which allows a relatively close fit of lid with the drum walls. A lid collar may be provided surrounding a central opening in lid. The drum includes a wall formed generally as a cylinder having top and bottom ends and is coated in the inside with a refractile material such as a mixture of graphite and zirconia oxide. In an example, the drum walls may be constructed of a plurality of individual pieces. For example, two half-shells may be joined together during carbonization chamber assembly. In such an example, the pieces may be joined according to a process appropriate for the material of construction of the pieces. For example, if walls are formed of metal, the pieces may be welded together.

Vents (pipes, air inlets) may be provided to extend through the drum walls between exterior and interior sides to provide inlets for accepting limited airflow into the carbonization chamber. Air vents allow outside air to enter the burn chamber and feed the fire. An external damper and/or blower pipes may be attached to the vents.

A constant speed blower may be provided at the outside end of the damper pipe that provides forced air that's varied by the damper and/or computer controller. In another example, a variable speed blower may be used without a damper. In yet another example, a damper may be used without any blower. Vents, in some embodiments, may also be used to pull a vacuum from the chamber or to introduce inert gasses such as nitrogen. Vents, in some embodiments, may also be used introduce catalysts or biological materials such as bacteria and fungi for the biological degradation stage of the process.

Any device of the invention described herein may include components with the following variations: The carbonization chamber can be made out of anti-rust metal, like stainless steel, preferably of cylindrical shape, which is a container that can withstand the heating and pressure conditions of the invention. The chamber is coated with refractile materials. An agitator system to mix the materials inside the carbonization chamber. A heating system or mechanism which can be powered from different energy sources, such as but not being limited to, electricity, gas, fuel oil, the carbon generated by the machine itself or other ways. Sufficient heat may be in the order of 1000 to 5000 W, preferably around 2000 W. A compressor and/or vacuum system, for example a compressor, which can ensure a working pressure of at least 5 down to 0.25 bars. A catalytic composition, which may be painted onto the internal walls of the chamber or introduced into the chamber. An inlet to supply or inject gasses, remove gasses or introduce catalysts or biological materials to aid in digestion and degradation. A dispensing port from which to extract the product. An outlet to release the water vapor or gas generated inside the carbonization chamber. Activated charcoal filters to remove the undesirable compounds and odors. Doors through which to fill the chamber with materials and extract the resulting carbon.

The invention has been described in this disclosure. However, it should be understood that this invention may take many different forms and thus should not be construed as being limited to the embodiment set forth herein. All publications mentioned herein are incorporated by reference for all purposes to the extent allowable by law. In addition, in the figures, identical numbers refer to like elements throughout. Additionally, the terms "a" and "an" as used herein do not denote a limitation of quantity, but rather denote the presence of at least one of the referenced items. The claims, disclosure and drawings of the present invention define but are not intended to limit the invention. All patents and publications disclosed herein are incorporated by reference to the fullest extent permissible by law.

"Food waste" is any organic material originally destined to be a comestible for humans of animals.

"Carbonization chamber" is any enclosure adapted for containing and heating food waste. It may be of any shape of dimensions but if frequently drum-shaped to allow rolling.

An "agitator system" is any system within the carbonization chamber designed to mix contents, generally comprising baffles within the drum.

The "heating system" is any system adapted to supply heat energy to the Carbonization chamber and may be powered by electricity, gas or oil. Because the carbonization process is exothermic, the heating system includes the carbonization chamber itself.

"Charcoal" is described as a carbonaceous solid with a fixed-carbon content of 70 wt % or more. The term "biomass" includes all sorts of woody and herbaceous plant material, such as wood logs, slabs, chips, and bark; and agricultural residues such as corncobs, corn stover, wheat straw, nutshells, and sugar cane bagasse. Biomass may also include the organic fraction of municipal solid wastes, sewage sludge, manure, or other excrement, and the residues of animal husbandry, such as bones and carcasses. The term "inert" in the context of the present invention means that such compound, composition or material does not react with biomass, or its byproducts of pyrolysis, at temperatures and pressures attained within the reaction container in the practice of the present invention.

The invention claimed is:

1. A high-efficiency food waste carbonization process comprising the following steps:
   (a) providing a carbonization device, the device comprising a filling hopper for providing feedstock to a drum, the drum defining an interior chamber surrounded by a heat insulating layer and having a door for filling and disgorging contents, the drum having interior baffles to aid mixing contents, wherein the drum is connected to a rotating drive shaft and the drive shaft is connected via a belt or gears to a motor, wherein the drum is effectively airtight when in use except for intentional introduction and extraction of fluids optionally via input lines and output lines, and wherein the device additionally includes a heating source for providing heat to the interior chamber of the drum, and a thermal probe within the drum to monitor an internal temperature, wherein said thermal probe is functionally connected to a thermostatic control unit which controls heat input and regulates the internal temperature of the drum, and wherein the device additionally includes a heat transfer system for transferring heat away from the drum and transferring said heat to an electric generator;
   (b) loading food waste materials through the door into the drum;
   (c) inoculating the food waste in the drum with a defined bacterial culture;
   (d) rotating the drum and heating and fermenting the contents of the drum at a temperature of between 25° C. and 45° C. for a fermentation time between 1 and 7 days;
   (e) using a vacuum pump to create a vacuum or partial vacuum within the drum;
   (f) maintaining a vacuum or partial vacuum within the drum between 0.01 and 0.50 atmospheres;
   (g) drying the contents within the drum under vacuum and heat for a drying time between 2 and 84 hours at a drying temperature between 100° C. and 450° C.;
   (h) continuing to maintain a vacuum within the drum or flooding the drum with nitrogen;
   (i) carbonizing the contents within the drum by heating the interior chamber of the drum to a temperature between 250° C. and 1200° C. to promote production of charcoal, and maintaining this temperature for between 1 and 72 hours;
   (j) cooling the drum and disgorging a charcoal product; and
   (k) grinding the charcoal product and forming it into shaped briquettes.

2. The process of claim 1, wherein the device further comprises a nitrogen plasma generator functionally connected to the drum.

3. The process of claim 1, wherein at step (c) the bacterial culture comprises *Bacillus subtilis* and/or *Pseudomonas* species.

4. The process of claim 1, wherein in step (d) the temperature is between 37° C. and 45° C.

5. The process of claim 4, wherein wherein the fermentation time is between 1 and 3 days.

6. The process of claim 1, wherein in step (g) the drying temperature is between 350° C. and 350° C.

7. The process of claim 6, wherein the drying time is between 12 and 24 hrs.

8. The process of claim 1, wherein in step (i) the interior chamber of the drum is heated to between 300° C. and 450° C. for between 6 and 48 hours.

9. The process of claim 1 wherein in step (i) the interior chamber of the drum is heated to between 900° C. and 1100° C.

10. The process of claim 1, wherein, in step (i), a plasma is generated within the drum to promote breakdown of complex molecules thereby aiding carbonization.

11. The process of claim 10, wherein the plasma is a nitrogen plasma.

12. The process of claim 1, wherein a plasma is introduced into the drum after step (b) and before step (c).

13. The process of claim 12, wherein a plasma is additionally introduced into the drum in step (i).

14. The process of claim 1, further comprising, at one of steps (b) or (c), adding a catalyst to the drum, said catalyst selected from a group consisting of: dicarboxylic acid, tricarboxylic acid and sulfuric acid.

15. The process of claim 1, further comprising, at one of steps (b) or (c), adding a catalyst to the drum, said catalyst selected from a group consisting of: palladium, rhodium, platinum, AlCl3-HCl, and a sulfonated porous carbon catalyst.

16. The process of claim 1, wherein the interior chamber of the drum is coated with graphite and/or zirconia oxide.

* * * * *